United States Patent [19]

Rutt et al.

[11] 4,255,664

[45] Mar. 10, 1981

[54] SPLIT FILTER CT

[75] Inventors: Brian K. Rutt; Aaron Fenster, both of Toronto, Canada

[73] Assignee: Picker Corporation, Cleveland, Ohio

[21] Appl. No.: 46,609

[22] Filed: Jun. 8, 1979

[30] Foreign Application Priority Data

Mar. 23, 1979 [CA] Canada .................................. 324189

[51] Int. Cl.³ ............................................. A61B 6/00
[52] U.S. Cl. .................................. 250/445 T; 250/510
[58] Field of Search ............................ 250/445 T, 510

[56] References Cited

U.S. PATENT DOCUMENTS 3,971,948  7/1976  Pfeiler et al. ..................... 250/445 T

OTHER PUBLICATIONS

McCullough, E. C., "Photon Attenuation in Computed Tomography", *Medical Physics*, vol. 2, No. 6, 1975.

Alvarez et al., "Energy-Selective Reconstructions in X-Ray Computerized Tomography", *Phys. Med. Biol.*, vol. 21, No. 5, 1976.

*Primary Examiner*—Alfred E. Smith
*Assistant Examiner*—T. N. Grigsby
*Attorney, Agent, or Firm*—Watts, Hoffmann, Fisher & Heinke Co.

[57] ABSTRACT

An improved computer assisted tomographic scanner is disclosed. The scanner includes a source of X-radiation and an array of detectors for determining X-ray intensity once that radiation has passed through a patient. The source emits a spread of radiation which is filtered to comprise a spread of two distinct energy ranges before the radiation reaches the patient. This filtering produces multiple intensity readings for a given X-ray path: thereby allowing imaging electronics within the scanner to reduce chromatic artifacts and provide electron density and atomic number mappings to the diagnostician.

17 Claims, 5 Drawing Figures

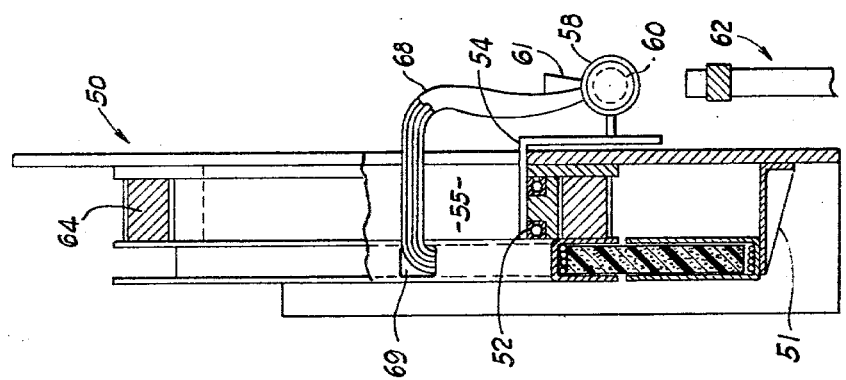
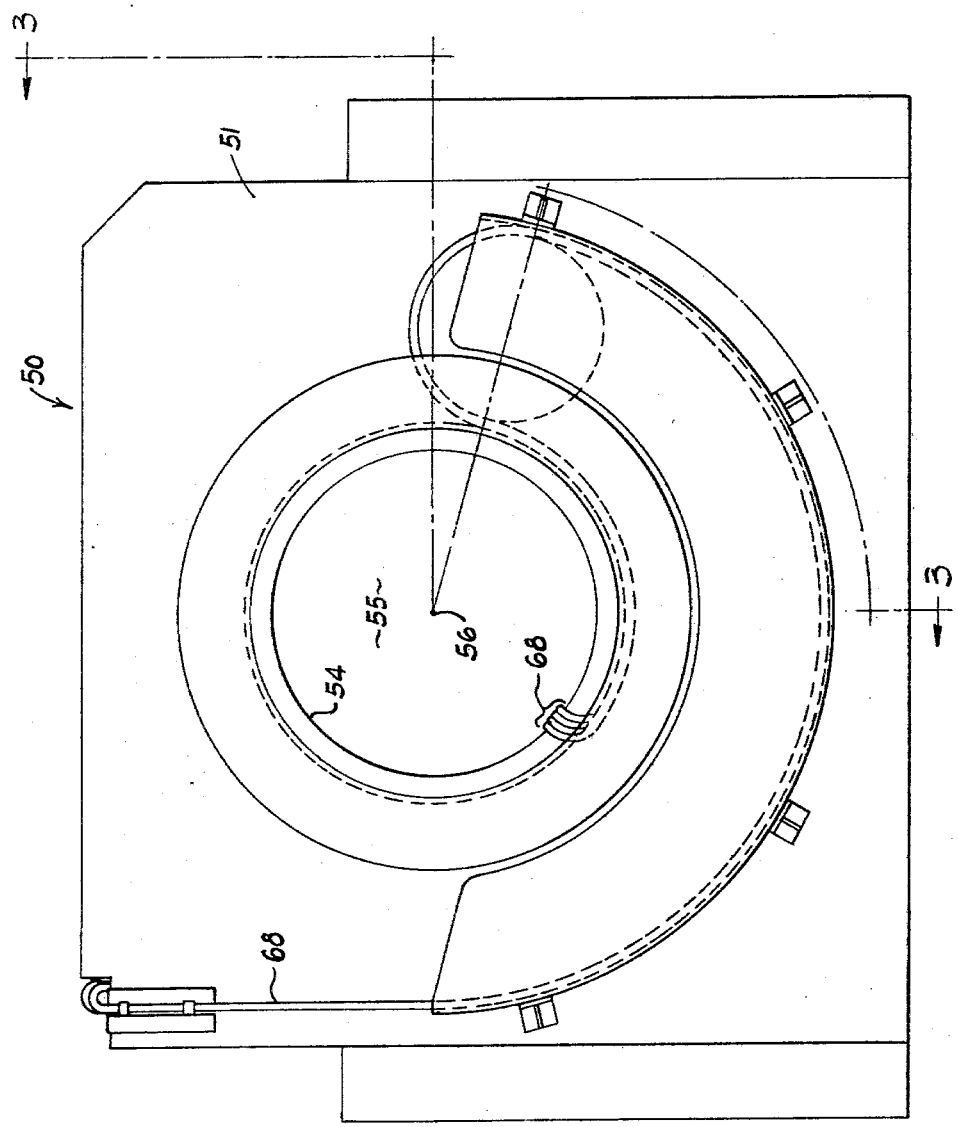

SPLIT FILTER CT

BACKGROUND OF THE INVENTION

1. Field of the Invention

This invention relates generally to a new method and apparatus for computed tomography scanning. More particularly, it relates to a new x-ray beam filtering technique useful for reducing adverse affects caused by chromatic artifacts.

2. Prior Art

In recent years the art of computed tomography scanning has enabled medical personnel to gain information about the internal structure of a patient that is not available with other procedures. A conventional radiograph is a two dimensional shadow image of a three dimensional subject. The depth dimension is not apparent because all interior portions of the patient are imaged in a single plane. As a consequence, a conventional radiograph often fails to show, in the direction of x-ray propagation, the spacial location of a condition existant within a patient.

In computed tomography, an image of a cross-sectional plane of a subject or patient is developed by sequentially directing radiation through the patient from a plurality of origins. Detectors are used to detect x-radiation intensity after it has passed through the patient. From these intensity values it is possible to reconstruct an image of the cross section of interest. Various reconstruction algorithms have been developed, each requiring intensity readings from a number of different orientations. These readings are modified according to those algorithms and transmitted to imaging electronics which provide a density mapping of the patient.

When the computed tomography reconstruction algorithm has been performed the diagnostician has available a representation of a patient cross section or slice which indicates variations in density within the patient. If a number of these slices of cross sections of the patient are obtained, the position and location of various organs and tissue can be analyzed with great precision.

CT Scanning apparatus has evolved from a so-called first generation CT Scanner to improved fourth generation scanners. The first generation scanner included one "pencil" beam source of x-rays and a single x-ray detector. The source-detector pair translated and rotated about the patient so this first generation scanner was called a translate-rotate (TR) machine. Second generation machines are T.R. machines with plural beams and detectors while third generation machines orbit a source and a set of detectors. Fourth generation machines include a stationary, annularly disposed, detector array comprising hundreds of individual detectors. One source of radiation rotates about the patient thereby irradiating the cross section of interest from a variety of positions. The stationary detectors transmit intensity data to the imaging electronics for reconstruction processing.

As the art of computed tomography scanning has matured, certain techniques for improving the CT image has been formulated. One improvement has been the reduction of various artifacts which degrade image quality. These artifacts typically appear as lines or streaks which suggests structure but which in fact correspond to no density variation within the patient. One such artifact or aberation is a so-called "chromatic artifact". Chromatic artifacts occur in the image due to the fact that the x-radiation emitted from the x-ray source comprises radiation of more than one energy. When x-radiation is emitted from an x-ray tube the range or distribution of energies comprises a skewed gaussian energy distribution. The skewing of the gaussian distribution is concentrated toward a low energy side so that many photons comprising the x-ray beam are concentrated about a mean energy and an exponentially decreasing number of photons have higher energies.

Examples of chromatic artifacts or aberations within computed tomography scanning are known. If a CT scan is made of a completely uniform body such as a cross section of water, the computed tomography reconstruction should show a uniform cross section representing the constant density of the water. In fact, when a computed tomography scan is taken of a uniform body such as water, the edge portions of this section appear lighter than the interior.

One useful CT application is a so-called brain scan. It is known from extrinsic examination that brain tissue is fairly uniform in density. It is also known that a CT scan of the brain tissue results in lighter image quality around the edge portions of the brain with darker interior portions. From the experience in scanning a water phantom, it is theorized, therefore, that the difference in density seen in a typical brain scan is a result of the non-monochromatic nature of the scanning radiation and not due to variations in brain tissue density.

The chromatic artifact problem also appears when bone structures are examined. In a scan of the human skull dark streaks appear between projections of bone. As is the case in brain tissue scanning, it is known that these dark streaks may not correspond to structural or density variations. If the doctor or medical researcher knows these streaks or variations are artifacts, he can take this factor into account when diagnosing. If, however, the doctor is examining a region about which he has no prior knowledge, these streaks and nonuniformities can confuse and hide the true structure and condition of the patient.

In addition to concern over artifact problems, research in CT scanning has been aimed at increasing the amount of useful information CT scanning procedure can provide. In addition to patient density data, it is now possible for the CT scan to provide a mapping of atomic number and electron density variations in the patient. As is known, the atomic number is variable depending upon the material comprising the particular cross section being scanned. The electron density is to some extent also dependent upon this material but also varies with the packing density and configuration of the material.

Electron density variation information is a valuable aid in radiation therapy. Recently developed calculations for the proper dosage required in cancer treatment require that the electron density within the area under radiation therapy be known to an accuracy of approximately 2 percent. Advances in the CT scanning technique have provided this degree of accuracy in electron density mapping and aided the radiotherapist to prescribe proper dosage treatments.

Knowledge regarding the atomic number variation within the patient can have significance in two important diagnostic areas. Knowledge concerning the atomic number variations can lead to differential diagnoses of tumors and cysts within the patient. Perhaps even more importantly, atomic number variations can prove important in injection contrast diagnostic procedures.

When an atomic number density variation image is created, the effects of injected agents such as iodine and xenon are magnified. This follows since the injected elements typically have atomic numbers much greater than the atomic numbers represented in human tissue. Since contrast injection procedures are frequently utilized in CT scanning, any enhancement of the visualization of such agents significantly aids diagnostic procedures.

Heretofore, proposals for chromatic artifact reduction and variation mappings of electron density and atomic number were achieved at the expense of slower scanning times and increased patient exposure to x-radiation. To provide the imaging electronics with enough information to reduce the artifacts and to diversify information available from a CT scan, prior proposals necessitated two CT scans for a given scanner position relative to the patient. One scan was conducted at a first average x-ray energy and then a second scan was conducted at a second energy different from the first scan energy. The intensity data from these two scans was then modified according to known data processing techniques to reduce artifacts and to yield the atomic number and electron density variation information.

SUMMARY OF THE INVENTION

The present invention features a new filtering technique which provides information necessary to the CT reconstruction process in such a way that chromatic artifacts are reduced and also provides the capability to create electron density and atomic number mappings. The invention allows these advantageous features to be achieved during one scan of a particular patient cross section and therefore obviates the need for multiple energy irradiation of that cross section.

Like other computed tomography scanners, the invention includes a source of x-rays, a series of detectors, means for moving the source relative to a patient, and reconstruction electronics for receiving intensity data from the detectors. The reconstruction electronics operate according to known algorithms which provide a mapping of density variations within the patient.

The present invention employs a special filtering arrangement which effectively provides multiple energy irradiation during a single CT scan. To appreciate how this improved filtering is accomplished, it should be understood that a typical tomography x-ray source emits a spread of individual x-ray beams of radiation which subtend a certain angle as x-rays are emitted from the source. To practice the invention, an asymetrical filter is placed in the path of x-radiation before that radiation strikes the patient. The asymety of the filter is about a centerline of the spread beams radiation. The filter can comprise either two separate materials or can include a single filter positioned so that only half of the beam is filtered by the single uniform composition material comprising that filter.

The invention can be practiced with any generation CT Scanner which includes a spread of radiation. One criteria necessary to fully enjoy the full advantages of the present invention on any CT Scanner, however, is the ability to scan at least 360° about the patient. That is, it is necessary that the source of X-radiation completely circumscribe the patient as radiation is emitted.

Due to the geometric configuration of the source, the filter, and the detectors, the improved asymetric filtering provides the imaging electronics with intensity data from two distinct x-radiation energy exposures during a single 360° scan of the patient. As the scan begins, detectors receiving radiation from one side of the spread beam receive attenuated radiation which has passed through a first side of the asymetric filter. At a later time in the scan, radiation passing through the other side of this filter traverses substantially the same path but due to the asymety of the filter the average radiation energy entering the patient is different. As will be discussed in a description of one preferred embodiment of the invention, this multiple intensity data for substantially identical beam paths provides the imaging electronics with enough information to reduce chromatic artifacts and to provide atomic number and electron density mappings of the patient.

From the above, it should be appreciated that one object of the invention is to provide sufficient computed tomography intensity data in a single CT scan to reduce image artifacts and to provide expanded CT imaging capabilities. Other features and objects of the invention will become better understood when the accompanying diagrams are considered in conjunction with the detailed description of a preferred embodiment of the invention.

BRIEF DESCRIPTION OF THE DRAWINGS

FIG. 2 is a rear elevational view of a stationary detector CT machine with its housing removed;

FIG. 3 is a section view of the CT Scanner of FIG. 2 as seen from the plane indicated by the line 3—3 of FIG. 2;

DETAILED DESCRIPTION OF A PREFERRED EMBODIMENT

Figure 1:
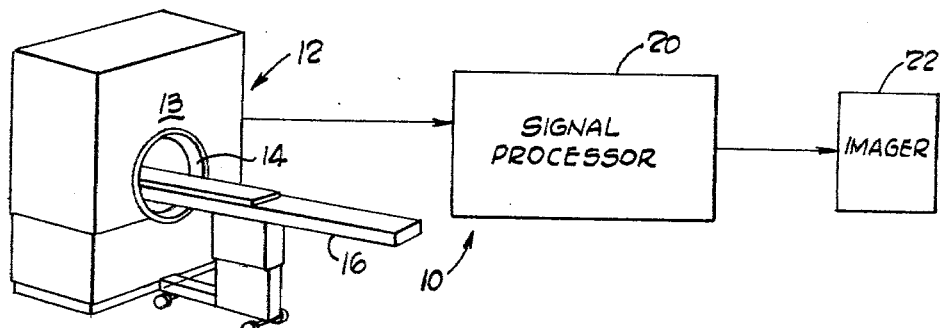
FIG. 1 is a schematic of a CT Scanning unit.

FIG. 1 shows a computed tomography system 10 used for examining the internal structure of a patient. The unit comprises a scanning unit 12, couch 16, signal processor 20 and imager 22. The scanning unit 12 is mounted to a floor and remains stationary relative to the patient. The scanning unit includes a housing 13 which covers x-ray apparatus and provides an attractive appearance. The housing 13 is constructed to include an aperture 14. The couch 16 is movably mounted and is operative to position the patient within the aperture 14 for x-ray scanning. The signal processor 20 and the imager 22 are electrically connected to the scanning unit. The scanning unit obtains x-ray intensity data and sends this intensity data to the signal processor. The x-ray intensity data is then processed by the signal processor to obtain information concerning the relative densities of a patient cross-section of interest. This density data is transferred to the imager where the doctor can view the relative density information on a viewing screen.

The present invention can be practiced with a translate/rotate, orbital, or stationary detector scanning unit. Details regarding the physical construction and operation of a translate/rotate scanning apparatus can be found in copending U.S. patent application Ser. No. 921,010 which has been assigned to the assignee of the present invention. Details regarding the construction and operation of an orbital scanning unit can be found in U.S. Pat. No. 3,983,399 also assigned to the assignee of the present invention.

Referring to FIGS. 2 and 3, an x-ray tube support and manipulating assembly comprising a stationary detector scanning unit is shown generally at 50. The stationary detector scanning apparatus is a so-called fourth generation CT device and has surpassed translate/rotate and orbital machines in use. The assembly 50 includes a housing and frame structure 51. A pair of spindle bearings 52 are carried by the housing and frame structure 51, (see FIG. 2). A tubular spindle 54 is journaled in the bearings 52. The spindle 54 delineates a patient receiving opening 55. When the scanner is in use, a patient is supported on a stretcher with portions of the patient's body disposed within the opening 55.

An x-ray tube assembly 58 (see FIG. 3) is fixed to the tubular spindle for orbital rotation about an axis 56 of the spindle 54 and the opening 55. The x-ray tube assembly includes an x-ray tube indicated by the dotted line 60, a collimator shown diagramically at 61, and other known and conventional components of an x-ray tube assembly of the type used in CT studies.

The tube support and manipulating assembly 50 shown in FIGS. 2 and 3 is of a machine of the stationary detector type. For clarity of illustration, and because the detector array is now known in the art, the annular detector array which is around the orbital path of the x-ray tube assembly 58 is not shown except in a fragmentary schematic way at 62 in FIG. 3.

In use, the x-ray tube is orbited about the axis 56 over a range of approximately 540°. This 540° range allows orbital motion over a path of sufficient length to accelerate the tube to its full speed for a study, a 360° scan and deceleration through an additional orbital path which is long enough to permit the tube to be smoothly brought to a stop. The orbital motion is first in one direction and then the other. Expressed another way, the tube may be moved a range of 540° in a clockwise direction and then 540° counterclockwise on the next study.

A drive for this orbital motion is shown schematically and it includes an annular motor 64 which is connected to the spindle 54. The drive shown is for schematic illustration only. Any of the known and commercially accepted drive systems can be employed.

Four flexible conduits or cables 68 are connected to the x-ray tube assembly 58. These cables include conductors for supplying power for the x-ray tube, for collimator and filter adjustment, and such other power requirements of the tube assembly may have. The cables 68 extend from the x-ray tube through the opening 55 where they are adjacent the spindle 54 and into a cable delivery opening 69 (see FIG. 3).

As will be discussed below, one criteria necessary to practice the present invention is that the scanning x-rays irradiate the patient from at least 360°. The disclosed SD machine does so, and a review of those references incorporated herein shows that both translate rotate and orbital machines also may be used to irradiate a patient through at least 360°.

Theory

The present invention provides a signal processor 20 (see FIG. 1) with enough information to generate a so-called "monoenergetic transmission" through the patient from which monchromatic density distribution mappings may be created. This technique eliminates the chromatic artifacts which heretofore reduced the effectiveness of CT scanning. The invention also supplies the signal processor with enough information to obtain electron density and atomic number mappings of the patient cross-section.

A method for obtaining the electron density, atomic number, and monochromatic density mappings is presented in a paper entitled "Energy Selective Reconstructions in X-Ray Computerized Tomography" by Robert E. Alvarez and Albert Macovski. Phys. med. Biol., 1976 Vol 21, No. 5. That paper is incorporated herein by reference. The Alvarez et al paper discusses a technique for modifying intensity readings obtained from CT scanning apparatus to obtain improved CT mappings. The basics of this technique are discussed below.

Various reconstruction algorithms are known for producing a density mapping of a patient cross-section. These algorithms utilize radiation intensity values which have been attenuated by interaction with the patient. The logarithm of a ratio of attenuated and unattenuated intensity readings for a typical detector on a typical path is known to correspond to the following line integral:

$$t = \int_l u(x,y) dl. \qquad 1$$

In this integral u(x,y) is an absorption function indicative of the density at the spacial location x,y. The line integral is evaluated for a variety of paths and the data obtained used in a reconstruction algorithms known in the art. These reconstruction techniques produce the mapping u(x,y). The mappings available through practice of the invention are also obtained by utilization of a similar reconstruction algorithm.

For a given patient cross-section, the distribution of attenuation coefficients, u is really also a function of energy. Thus, the attenuation data can be thought of as a three dimensional function: u(x,y;E), where x and y are the coordinates of the patient cross-section and E is the photon irradiation energy.

For x-ray energies used in CT scanning, essentially two attenuation processes occur. These two attenuation processes are the photoelectric and compton absorption phenomena. Due to this fact the function u can be written as a sum of these two effects as follows:

$$u(x,y;E) = kE^{-3.2} p(x,y)[\bar{Z}(x,y)]^{3.8} + \sigma(E)p(x,y) \qquad 2$$

where k is equal to $9.8 \times 10^{-24}$ and $\sigma(E)$ is the Klien-Nishina coefficient. p(x,y) is the electron density distribution and Z(x,y) is the average atomic number distribution. This relation is known within the art.

Using the notation $a_t(x,y) = p(x,y)[\bar{z}(x,y)]^{3.8}$ and $a_c(x,y) = p(x,y)$ this equation simplfies to:

$$u(x,y;E) = kE^{-3.2} a_t + \sigma(E) a_c. \qquad 3$$

The quantities $a_t$ and $a_c$ are respectively the energy independent parts of the photoelectric and compton coefficients. A plot of these functions represents the spacial variations of atomic number and electron density. One aim of the invention therefore is to produce a representation of $a_t$ and $a_c$. To appreciate how this is accomplished, it should be recalled how the mapping of u(x,y) was obtained. It was known that the line integral of u(x,y) over the beam path was equal to the logarithm of an attenuated and unattenuated intensity and with multiple intensity reading u(x,y) could be reconstructed. Similarly if one wishes to reconstruct $a_t$ and $a_c$ one should be able to take a line integral of these functions over a beam path to obtain $$A_t = \int_l a_t(x,y) \, dl \quad \quad 4$$

and $$A_c = \int_l a_c(x,y) \, dl \text{ for each beam path.}$$

It is known that if two intensity readings are obtained from a single x-ray path using two values of x-ray source energy, values for $A_t$ and $A_c$ can be determined for that path. A rigorous determination of $A_t$ and $A_c$ is complex but an approximation exists for solving rather simply for $A_t$ and $A_c$.

To use this approximation technique it is useful to define two attenuation coefficients:

$$t_L = \ln \frac{(I_{oL})}{(I_L)} \text{ and } t_H = \ln \frac{(I_{oH})}{(I_H)}.$$

$I_{oL}$ is the unattenuated low energy beam intensity, $I_{oH}$ is the unattenuated high energy beam intensity, and $I_L$, $I_H$ are attenuated beam intensities. Using these conventions it is possible to express $A_c$ and $A_t$ as a power series of $t_L$ and $t_H$. Thus;

$$A_c = \\ a_1 t_L + a_2 t_L^2 + a_3 t_L^3 + a_4 t_H + a_5 t_H^2 + a_6 t_H^3 + \text{cross terms} \quad 6$$

and $$A_t = \\ b_1 t_L + b_2 t_L^2 + b_3 t_L^3 + b_4 t_H + b_5 t_H^2 + b_6 t_H^3 + \text{cross terms} \quad 7$$

where $a_1, a_2, a_3 \ldots$ and $b_1, b_2, b_3 \ldots$ etc are constants which can be determined from calculations of $A_c$ and $A_t$ using phantoms of known density and geometry. Once these constants are determined using a least square fit, $A_t$ and $A_c$ can be evaluated for unknown geometries and configurations using calculations of $t_L$ and $t_H$ obtained from the intensity readings. Once the $A_t$ and $A_c$ figures are known, standard reconstruction techniques yield the two functions $a_t(x,y)$ and $a_c(x,y)$. As noted, these functions are proportional to electron density and average atomic number at the spatial location, x,y.

Monochromatic density information can also be obtained by using the double energy readings required to formulate $A_t$ and $A_c$. Integrating equation 3 over the path length of a given X-ray path yields:

$$t_m = \int_l u(x,y;E) \, dl = kE^{-3.2} A_t + \sigma(E) A_c. \quad 8$$

Since $A_t$ and $A_c$ are known (or can be calculated from the multiple intensity readings), it is possible to evaluate $E^{-3.2}$ and $0(E)$ for an average energy of emission to obtain $$t_m = \int_l u(x,y;E^*) \, dl.$$

where $E^*$ is the average energy of the scanning radiation. This value of $t_m$ is obtained for a number of different radiation paths in the usual manner and the reconstruction techniques are then used to plot $u(x,y;E^*)$ which is a monochromatic density representation without chromatic artifacts.

From the above it is apparent that to achieve this objects set forth previously, two readings are required for each irradiation path. Using the terminolgy introduced previously, the path must be irradiated with a high energy source and a low energy source so that the values $t_H$ and $t_L$ may be calculated for each path. This information is then used to calculate $A_t$ and $A_c$ and then $a_c(x,y)$, $a_t(x,y)$, and $u(x,y;E^*)$.

Figure 4:
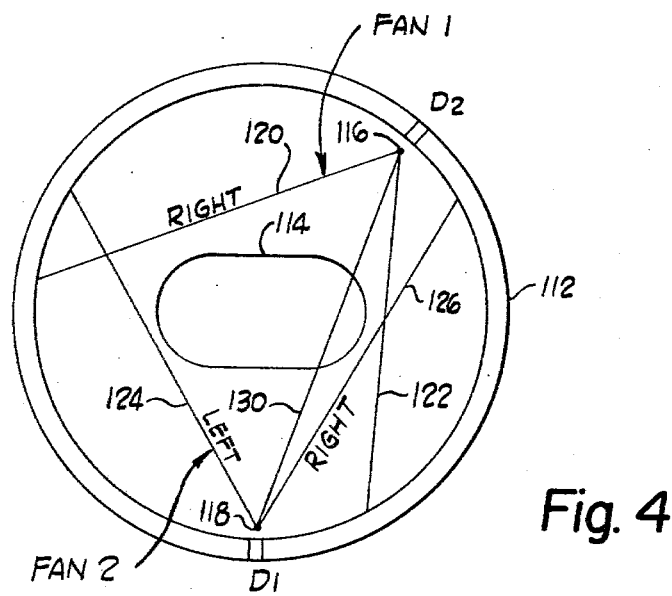
FIG. 4 is a schematic representation of a source and detector arrangement used in CT Scanning.
Figure 5:
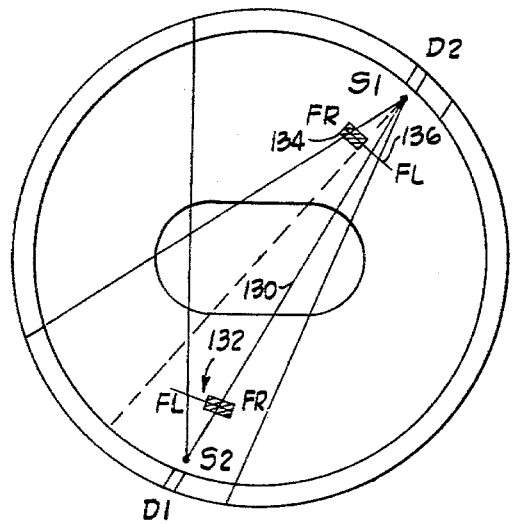
FIG. 5 is a representation similar to FIG. 4 representation in which a split filter has been added.

FIGS. 4 and 5 illustrate how multiple intensity readings during a single scan are obtained through utilization of the present invention. FIG. 4 shows an annular array of detectors 112 positioned about a patient cross-section 114. Two positions, 116, 118 indicate two different source orientations for irradiating that cross-section.

During its rotation about the patient, the source continually emitts a spread of radiation which traverses the patient cross-section. When the source is at a first position 116, the boundaries of that spread 120, 122 subtend the complete patient cross-section. Similarly, when the source has been repositioned to a second position 118, the boundaries of that spread 124, 126 also subtend the whole patient cross-section.

The illustration of the two beam positions shows that a radiation path 130 exists within the fan or spread which traverses a substantially identical path at two different times during the CT scan. When the source is at a first position 116, a first detector D1 records intensity data for that path. Later, when the source has been moved to a second position 118, a second detector D2 records intensity readings for that path.

The geometry of the spread or fan beam is such that when the path 130 is first irradiated (that is when the source was at a first position 116) it comprises a portion of the left-hand side of the spread. Later, after the source has moved to a second position 118, the path 130 comprises a portion of the right-hand portion of the spread. It should be apparent that for any two opposite source positions the two coincident rays or paths originate from opposite sides of the fan or spread of radiation.

If a filter FR is fixed to the x-ray source covering the right half of the fan or spread of radiation, and a different filter FL is placed over the left half of the fan, it follows that every pair of opposing rays will be transmitted through both the right and left hand sides of the filter and therefore dual energy information will be obtained. Reference is now made to FIG. 5 which illustrates a filter 132 mounted between the source and the patient cross-section which divides the spread or fan beam of radiation into two portions. A first or right-hand portion is filtered by a first filter 134 and the second or left-hand portion of the beam is filtered by a second filter 136. By constructing the filter from two different materials or from the same material but from different thicknesses, the effective beam energy will be different for the two halves of the beam. In this way dual energy information is obtained during a single scan. When the source is a first position 116 the common paths 130 is irradiated by radiation which is passed through the left-hand filter 136. At a later time in this scan when the source is at a position 118 that same path 130 is irradiated by radiation passing through the right-hand filter 134.

The two intensity readings from the detectors in these two configurations are then utilized to generate the two constants $A_c$ and $A_t$ as discussed previously.

Thus, by dividing a filter into two portions, one of which is thicker or of a different material than the other, multiple intensity readings are obtained using beam energy of differing values in one single scan of the patient cross-section. Possible adverse effects due to patient motion are minimized and multiple information mappings can be obtained using this multiple energy information.

Optimum filter design is based upon minimizing noise in either $A_c$, $A_t$ or $t_m$. To determine optimum filter designs noise studies have been made using the following generalized formulation:

$t_L$ is a function of $A_t$, $A_c$
$t_H$ is a function of $A_t$, $A_c$ $$\Delta t_L = \frac{\partial t_L}{\partial A_t}\bigg|_{A_bA_c} \Delta A_t + \frac{\partial t_L}{\partial A_c}\bigg|_{A_bA_c} \Delta A_c \quad 9$$

$$\Delta t_H = \frac{\partial t_H}{\partial A_t}\bigg|_{A_bA_c} \Delta A_t + \frac{\partial t_H}{\partial A_c}\bigg|_{A_bA_c} \Delta A_c \quad 10$$

Setting:

$$m_{11} = \frac{\partial t_1}{\partial A_T}\bigg|_{A_bA_c}; \; m_{12} = \frac{\partial t_1}{\partial A_c}\bigg|_{A_bA_c}; \; m_{21} = \frac{\partial t_H}{\partial A_t}\bigg|_{A_bA_c};$$

$$m_{22} = \frac{\partial t_H}{\partial A_c}\bigg|_{A_bA_c}$$

Then:

$$\Delta t_L = m_{11}\Delta A_t + m_{12}\Delta A_c \quad 11$$

$$\Delta t_H = m_{21}\Delta A_t + m_{22}\Delta A_c \quad 12$$

Solving:

$$\Delta A_t = \frac{m_{22}\Delta t_L - m_{12}\Delta t_H}{D}$$

$$\Delta A_c = \frac{m_{11}\Delta t_H - m_{21}\Delta t_L}{D}$$

$$D = m_{11}m_{22} - m_{12}m_{21}$$

Obtaining the variance or noisiness of the above expressions, (noting that $t_L$ and $t_H$ are statistically independent), one has:

$$\sigma^2_{A_t} = \left(\frac{m_{22}}{D}\right)^2 \sigma^2_{tL} + \left(\frac{m_{12}}{D}\right)^2 \sigma^2_{tH} \quad 13$$

$$\sigma^2_{A_c} = \left(\frac{m_{11}}{D}\right)^2 \sigma^2_{tH} + \left(\frac{m_{21}}{D}\right)^2 \sigma^2_{tL} \quad 14$$

but $t_L = \ln(I_{oL}/I_L)$ $$\sigma^2_{tL} = \left|\frac{dt_L}{dI_L}\right|^2 \sigma^2_{IL} = \frac{\sigma^2_{IL}}{I_L^2} \quad 15$$

$$\& \; \sigma^2_{tH} = \frac{\sigma^2_{IH}}{I_H^2} \quad 16$$

Therefore:

$$\sigma^2_{A_t} = \left(\frac{m_{22}}{D}\right)^2 \left(\frac{\sigma_{IL}}{I_L}\right)^2 + \left(\frac{m_{12}}{D}\right)^2 \left(\frac{\sigma_{IH}}{I_H}\right)^2 \quad 17$$

$$\sigma^2_{A_c} = \left(\frac{m_{11}}{D}\right)^2 \left(\frac{\sigma_{IH}}{I_H}\right)^2 + \left(\frac{m_{21}}{D}\right)^2 \left(\frac{\sigma_{IL}}{I_L}\right)^2 \quad 18$$

From knowledge of incident spectra, filter thickness and material, patient thickness and material, and detector response, it is possible to calculate all of the right hand quantities in equations (17) and (18). The method of optimization is therefore:

(1) pick filter design
(2) calculate $\sigma_{A_t}^2$, $\sigma_{A_c}^2$ as in (17), (18)
(3) plot these values versus filter design and repeat steps (1) and (2) until optimum (minimum noise) filter is found.

Filter optimization with respect to $t_m$ is similar.

$$t_m = f_t A_t + \sigma_c A_c; \text{ where } f_t = kE^{-3.2}$$

$$\sigma_{tm}^2 = f_t^2 \sigma_{A_t}^2 + \sigma^2 \sigma_{A_c}^2 + 2f_t\sigma(\overline{A_tA_c} - \overline{A_t}\,\overline{A_c}) \quad 19$$

Note: $A_c$ and $A_t$ are *not* independent so must calculate correlation term $\overline{A_tA_c} - \overline{A_t}\,\overline{A_c}$ $$\overline{A_tA_c} - \overline{A_t}\,\overline{A_c} = -\left(\frac{m_{11}m_{12}\sigma^2_{tH} + m_{21}m_{22}\sigma^2_{tL}}{D^2}\right)$$

obtained from equations (8) and (9) and using $$A_c = \overline{A_c} + \Delta A_c$$

$$A_t = \overline{A_t} + \Delta A_t$$

$$= \sigma^2_{tm} = f_t^2 \sigma^2_{A_t} + \sigma^2 \sigma^2_{A_c} -$$

$$2f_t\sigma\left(\frac{m_{11}m_{12}\sigma^2_{tH} + m_{21}m_{22}\sigma^2_{tL}}{D^2}\right)$$

This equation is again used to calculate noise for various filter designs, patient thicknesses and recombination energies.

Various filter designs are possible. One side of the fan beam may, for example, comprise air and the other side may be filtered by one of a number of materials. Alternatively both sides of the fan may be filtered by the same material but by different thicknesses. It should be apparent therefore to one skilled in the art that various modifications and alterations may be made without departing from the spirit or scope of the present invention as set forth in the appended claims.

What is claimed is:

1. A tomographic system comprising:
   (a) a source of x-radiation for irradiating a patient with an x-ray beam;
   (b) a plurality of detectors for detecting intensity of radiation emitted by the source;
   (c) drive means for moving the source in relation to the patient and thereby irradiating the patient from a plurality of orientations;
   (d) imaging electronics for modifying the detected intensity values and for reconstructing an image of an interior portion of the patient using the modified intensity values; and,
   (e) filter means, asymmetric about a beam centerline for selectively attenuating the x-ray beam.

2. The system of claim 1 wherein the filter means is mounted for motion with the source and is positioned between the source and the patient.

3. The apparatus of claim 2 wherein the filter means comprises two portions, each portion constructed from a different material to provide multiple beam energy portions.

4. A tomographic system comprising:

(a) a source of x-radiation for irradiating a patient with a spread shaped x-ray beam; said beam expanding from a narrow region to subtend an angle;

(b) a plurality of detectors for detecting intensity of radiation emitted by the source;

(c) drive means for moving the source relation to the patient and thereby irradiating the patient from a plurality of orientations;

(d) imaging electronics for modifying the detected intensity values and for reconstructing an image of an interior portion of the patient using the modified intensity values; and, (e) filter means, positioned to intercept half of said spread shaped beam.

5. The system of claim 1 wherein the filter means is mounted for motion with the source and is positioned between the source and the patient.

6. A method in tomographic scanning comprising the steps of:

(a) providing a source of x-radiation in proximity to a patient;

(b) moving the source about the patient, thereby irradiating the patient with beams of radiation from a number of locations;

(c) interposing a beam attenuating filter between the source and the patient, said filter being asymmetrical about a centerline of the x-ray beam;

(d) detecting the intensity values of said beam after passage through the patient;

(e) modifying said detected intensity values to form modified intensity values; and, (f) using said modified intensity values to create a cross sectional representation of the patient's structure according to a reconstruction algorithm.

7. The method of claim 6 where in moving the source about the patient said source completely circumscribes said patient and provides at least 360 degrees of scanning coverage.

8. The method of claim 7 which further comprises the step of calculating electron density distributions within the patient using intensity values for substantially identical beam paths which have been attenuated by different halves of the attenuating filter.

9. The method of claim 8 wherein the attenuating characteristics of the two filter halves are optimized to minimize the noisiness of a line integral of the electron density along said substantially identical beam paths.

10. The method of claim 7 which further comprises the step of calculating atomic number mappings of a patient cross section using multiple intensity readings from substantially identical beam paths which have been attenuated by the two halves of the attenuating filter.

11. The method of claim 10 wherein the attenuating characteristics of the two filter halves are optimized to minimize the noisiness of a line integral of the atomic number along said substantially identical beam paths.

12. The method of claim 7 wherein the attenuating filter provides multiple beam intensities for substantially identical beam paths during the tomographic scanning and wherein said modified intensity values are used to calculate monochromatic density information for a patient cross section.

13. The method of claim 12 wherein the attenuating characteristics of the two filter halves are optimized to minimize the noisiness of a line integral of the density function along said substantially identical beam paths.

14. A method in tomographic scanning comprising the steps of:

(a) providing a source of x-ray radiation in proximity to a patient;

(b) interposing a beam attenuating filter between the source and the patient, said filter being asymmetrical about a centerline of the x-ray beam;

(c) moving the source about the patient, thereby irradiating the patient with beams of radiation from a number of locations; said beams intercepting a patient cross section;

(d) detecting multiple intensity values from substantially identical beam paths; one intensity value from a beam passing through a first filter half and a second intensity value from a beam path passing through a second filter half;

(e) calculating a line integral of a spatially dependent electron density function for said substantially identical beam paths using said multiple intensity values; and (f) reconstructing the electron density function for the cross section from the line integral calculations using a reconstruction algorithm;

15. A method in tomographic scanning comprising the steps of:

(a) providing a source of x-ray radiation in proximity to a patient;

(b) interposing a beam attenuating filter between the source and the patient, said filter being asymmetrical about a centerline of the x-ray beam;

(c) moving the source about the patient thereby irradiating the patient with beams of radiation from a number of locations; said beams intercepting a patient cross section;

(d) detecting multiple intensity values from substantially identical beam paths; one intensity value from a beam path passing through a first filter half and a second intensity value from a beam path passing through a second filter half;

(e) calculating a line integral of a spatially dependent atomic number function for said substantially identical beam paths using said multiple intensity values; and (f) reconstructing the atomic number function for the cross section from the line integral calculations using a reconstruction algorithm.

16. A method in tomographic scanning comprising the steps of:

(a) providing a source of x-ray radiation in proximity to a patient;

(b) interposing a beam attenuating filter between the source and the patient, said filter being asymmetrical about a centerline of the x-ray beam;

(c) moving the source about the patient thereby irradiating the patient with beams of radiation from a number of locations; said beams intercepting a patient cross section;

(d) detecting multiple intensity values from substantially identical beam paths; one intensity value from a beam path passing through a first filter half and a second intensity value from a beam path passing through a second filter half; said halves chosen to have attenuating characteristics which minimize the noisiness of a line integral of the electron density along said substantially identical beam paths;

(e) calculating said line integral for said substantially identical beam paths using said multiple intensity values; and (f) reconstructing an election density function for the cross section from the line integral calculations using a reconstruction algorithm.

17. A method in tomographic scanning comprising the steps of:
(a) providing a source of x-ray radiation in proximity to a patient;
(b) interposing a beam attenuating filter between the source and the patient, said filter being asymmetrical about a centerline of the x-ray beam;
(c) moving the source about the patient thereby irradiating the patient with beams of radiation from a number of locations; said beams intercepting a patient cross section;
(d) detecting multiple intensity values from substantially identical beam paths; one intensity value from a beam path passing through a first filter half and a second intensity value from a beam path passing through a second filter half; said halves chosen to have attenuating characteristics which minimize the noisiness of a line integral of the atomic number along said substantially identical beam paths;
(e) calculating said line integral for said substantially identical beam paths using said multiple intensity values; and
(f) reconstructing an atomic number function for the cross section from the line integral calculations using a reconstruction algorithm.

* * * * *